(12) United States Patent
Petersson et al.

(10) Patent No.: US 7,228,159 B2
(45) Date of Patent: Jun. 5, 2007

(54) OPTICAL SENSOR CONTAINING PARTICLES FOR IN SITU MEASUREMENT OF ANALYTES

(75) Inventors: Bo Petersson, Rungsted Kyst (DK); Jesper Kristensen, Virum (DK)

(73) Assignee: Precisense A/S, Horsholm (DK)

( * ) Notice: Subject to any disclaimer, the term of this patent is extended or adjusted under 35 U.S.C. 154(b) by 528 days.

(21) Appl. No.: 10/483,426

(22) PCT Filed: Jun. 27, 2002

(86) PCT No.: PCT/EP02/07108

§ 371 (c)(1),
(2), (4) Date: Jan. 12, 2004

(87) PCT Pub. No.: WO03/006992

PCT Pub. Date: Jan. 23, 2003

(65) Prior Publication Data

US 2004/0199062 A1    Oct. 7, 2004

(30) Foreign Application Priority Data

Jul. 10, 2001    (GB) ................... 0116853.3

(51) Int. Cl.
*A61B 5/00*    (2006.01)
(52) U.S. Cl. .................. 600/316; 600/310; 600/317
(58) Field of Classification Search ........... 600/310, 600/312, 316, 317, 322
See application file for complete search history.

(56) References Cited

U.S. PATENT DOCUMENTS

| | | | |
|---|---|---|---|
| 3,996,345 A | 12/1976 | Ullman et al. | |
| 4,344,438 A | 8/1982 | Schultz | |
| 5,342,789 A * | 8/1994 | Chick et al. | 600/322 |
| 5,628,310 A * | 5/1997 | Rao et al. | 600/317 |
| 6,002,817 A * | 12/1999 | Kopelman et al. | 385/12 |
| 6,011,984 A * | 1/2000 | Van Antwerp et al. | 600/317 |
| 6,163,714 A | 12/2000 | Weber et al. | |
| 6,366,793 B1 * | 4/2002 | Bell et al. | 600/317 |
| 6,383,767 B1 * | 5/2002 | Polak | 435/14 |

FOREIGN PATENT DOCUMENTS

| | | |
|---|---|---|
| WO | WO 91/09312 | 6/1991 |
| WO | 97/19188 A | 5/1997 |
| WO | WO 97/19188 | 5/1997 |
| WO | WO 00/02048 | 1/2000 |
| WO | 00/47236 A | 8/2000 |

OTHER PUBLICATIONS

Wilkins et al, Med. Eng. Phys. (1996) vol. 18, No. 4, pp. 273-288.
Jaremko et al, Diabetes Care 1998 vol. 21, No. 3, pp. 444-450.
Meadows et al, Anal. Chem. Acta (1993) 280: pp. 21-30.
Fogt, Clin. Chem. 36/8(B), 1573-1580 (1990).
Atanasov et al, Med. Eng. Phys., vol. 18, No. 8, pp. 632-640, 1996.
Russell et al, Analytical Chemistry, vol. 71, No. 15, pp. 3126-3132, 1999.
Ballerstadt et al, Analytica Chimica Acta, 345 (1997) 203-212.
Lakowicz et al, Analytica Chimica Acta, 271 (1993) 155-164.
Tyagi et al, Nature Biotechnology (1998) vol. 16: p. 49.
Jeong et al, Nature 388: pp. 860-862, Aug. 1997.
Clark et al; "Optical Nanosensors for Chemical Analysis Inside Single Living Cells. I. Fabrication Characterization, and Methods for Intracellular Delivery of Pebble Sensors"; Analytical Chemistry, American Chemical Society Columbus, US, vol. 71, No. 21, Nov. 1, 1999, pp. 4831-4836, XP000898460.

* cited by examiner

*Primary Examiner*—Eric F. Winakur
(74) *Attorney, Agent, or Firm*—Nixon & Vanderhye P.C.

(57) ABSTRACT

The invention relates to a sensor for the in vivo measurement of an analyte, comprising a plurality of particles of suitable size such that when implanted in the body of a mammal the particles can be ingested by macrophages and transported away from the site of implantation, each particle containing the components of an assay having a readout which is an optical signal detectable transdermally by external optical means, and either each particles being contained within a biodegradable material preventing ingestion by the macrophages, or each particle being non-biodegradable. The invention relates to a process for the detection of an analyte using such a sensor, comprising implantation of the sensor into the skin of a mammal, transdermal detection of analyte using external optical means, degradation of the biodegradable material, ingestion of the particles by macrophages, and removal of the particles from the site of implantation by macrophages.

11 Claims, 2 Drawing Sheets

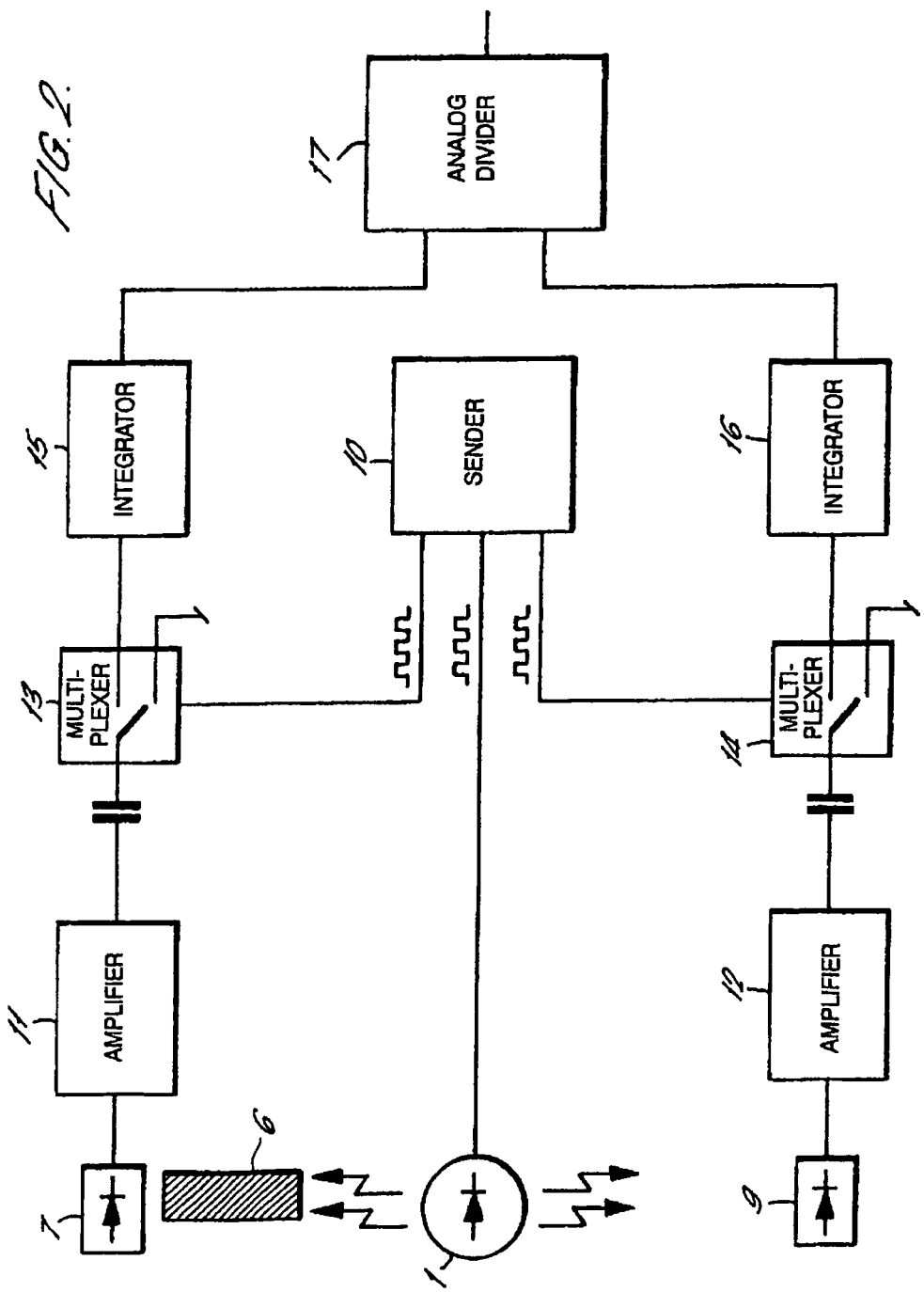

OPTICAL SENSOR CONTAINING PARTICLES FOR IN SITU MEASUREMENT OF ANALYTES

CROSS-REFERENCE TO RELATED APPLICATIONS

This application is the US national phase of international application PCT/EP02/07108 filed in English on 27 Jun. 2002, which designated the US. PCT/EP02/07108 claims priority to GB Application No. 0116853.3 filed 10 Jul. 2001. The entire contents of these applications are incorporated herein by reference.

The present invention relates to a sensor for use in the measurement or monitoring of analytes in body fluid using optical techniques. The sensor is particularly suitable for use in situations in which analyte levels must be closely monitored, for example with drugs that must be maintained within a narrow therapeutic window or where analyte measurements must be taken repeatedly, such as in diabetes management.

BACKGROUND OF THE INVENTION

In the management of diabetes, the regular measurement of glucose in the blood is essential in order to ensure correct insulin dosing. Furthermore, it has been demonstrated that in the long term care of the diabetic patient better control of the blood glucose levels can delay, if not prevent, the onset of retinopathy, circulatory problems and other degenerative diseases often associated with diabetes. Thus there is a need for reliable and accurate self-monitoring of blood glucose levels by diabetic patients.

Currently, blood glucose is monitored by diabetic patients with the use of commercially available calorimetric test strips or electrochemical biosensors (e.g. enzyme electrodes), both of which require the regular use of a lancet-type instrument to withdraw a suitable amount of blood each time a measurement is made. On average, the majority of diabetic patients would use such instruments to take a measurement of blood glucose twice a day. However, the US National Institutes of Health recently recommended that blood glucose testing should be carried out at least four times a day, a recommendation that has been endorsed by the American Diabetes Association. This increase in the frequency of blood glucose testing imposes a considerable burden on the diabetic patient, both in terms of financial cost and in terms of pain and discomfort, particularly in the long-term diabetic who has to make regular use of a lancet to draw blood from the fingertips. Thus, there is clearly a need for a better long-term glucose monitoring system that does not involve drawing blood from the patient.

There have been a number of recent proposals for glucose measurement techniques that do not require blood to be withdrawn from the patient. Various attempts have been made to construct devices in which an enzyme electrode biosensor is placed on the end of a needle or catheter which is inserted into a blood vessel (Wilkins, E. and Atanasov, P, Med. Eng. Phys (1996) 18: 273–288). Whilst the sensing device itself is located within a blood vessel, the needle or catheter retains connection to the external environment. In practice, such devices are not suitable for use in human patients first because the insertion of a needle or catheter into a blood vessel poses an infection risk and is also uncomfortable for the patient and hence not suitable for continuous use. Secondly, devices of this type have not gained approval for use in patients because it has been suggested that the device itself, on the end of a needle or catheter, may be responsible for the shedding of thromboses into the patient's circulation. This obviously poses a very serious risk to the patient's health.

Mansouri and Schultz (Biotechnology 1984), Meadows and Schultz (Anal. Chim. Acta. (1993) 280: pp 21–30) and U.S. Pat. No. 4,344,438 all describe devices for the in situ monitoring of low molecular weight compounds in the blood by optical means. These devices are designed to be inserted into a blood vessel or placed subcutaneously but require fibre-optic connection to an external light source and an external detector. Again the location of these devices in a blood vessel carries an associated risk of promoting thromboses and in addition, in one embodiment the need to retain a fibre-optic connection to the external environment is impractical for long-term use and carries a risk of infection.

In the search for a less invasive glucose monitoring technique some attention has also been focussed on the use of infra-red spectroscopy to directly measure blood glucose concentration in blood vessels in tissues such as the ear lobe or finger tip which are relatively "light transparent" and have blood vessels sited close to the surface of the skin (Jaremko, J. and Rorstad, O. Diabetes Care 1998 21: 444–450 and Fogt, E. J. Clin. Chem. (1990) 36: 1573–80). This approach is obviously minimally invasive, but has proven to be of little practical value due to the fact that the infra-red spectrum of glucose in blood is so similar to that of the surrounding tissue that in practical terms it is virtually impossible to resolve the two spectra.

It has been observed that the concentration of analytes in subcutaneous fluid correlates with the concentration of said analytes in the blood, and consequently there have been several reports of the use of glucose monitoring devices which are sited in a subcutaneous location. In particular, Atanasov et al. (Med. Eng. Phys. (1996) 18: pp 632–640) describe the use of an implantable glucose sensing device (dimensions 5.0×7.0×1.5 cm) to monitor glucose in the subcutaneous fluid of a dog. The device consists of an amperometric glucose sensor, a miniature potentiostat, an FM signal transmitter and a power supply and can be interrogated remotely, via antenna and receiver linked to a computer-based data acquisition system, with no need for a connection to the external environment. However, the large dimensions of this device would obviously make it impractical for use in a human patient.

Ryan J. Russell et al, Analytical Chemistry, Vol. 71, Number 15, 3126–3132 describes an implantable hydrogel based on polyethyleneglycol containing fluorescein isothiocyanate dextran (FITC-dextran) and tetramethylrhodamine isothiocyanate concavalin A chemically conjugated to the hydrogel network for dermal implantation. The implanted hydrogel spheres are to be transdermally interrogated.

R. Ballerstadt et al, Analytica Chemica Acta, 345 (1997), 203–212 discloses an assay system in which two polymer (dextran) molecules are respectively labelled with first and second fluorophores and are bound together by multivalent lectin molecules, producing quenching. Glucose saturates the binding sites of the lectin, causing disassociation of the two polymers, giving an increase in fluorescence.

Joseph R. Lakowicz et al, Analytica Chimica Acta, 271, (1993), 155–164 describes the use of phase modulation fluorimetry. This substitutes a fluorescence lifetime based measurement for the fluorescence intensity based measurements taught in the earlier described art.

Fluorescence lifetime can be measured by a phase modulation technique by exciting fluorescence using light which is intensity modulated at 1 to 200 MHz and measuring the phase shift of the emission relative to the incident light and the modulation of the emission.

In WO91/09312 a subcutaneous method and device is described that employs an affinity assay for glucose that is interrogated remotely by optical means. In WO97/19188 a further example of an implantable assay system for glucose is described which produces an optical signal that can be read remotely. The devices described in WO91/09312 and WO97/19188 will persist in the body for extended periods after the assay chemistry has failed to operate correctly and this is a major disadvantage for chronic applications. Removal of the devices will require a surgical procedure.

WO00/02048 deals with this problem by using a biodegradable material to contain the assay reagents. There the assay materials would be likely to be in contact with the bloodstream once the biodegradable material has degraded. It would be desirable to minimise or avoid this.

There remains a clear need for sensitive and accurate blood glucose monitoring techniques which do not require the regular withdrawal of blood from the patient, which do not carry a risk of infection or discomfort and which do not suffer from the practical disadvantages of the previously described implantable devices.

BRIEF DESCRIPTION OF THE DRAWINGS

The present invention will be further understood with reference to the following non-limiting examples, together with the accompanying figures in which:

FIG. 2 is a schematic diagram of a driver/amplifier circuit used in conjunction with the optical part of the fibre optic fluorimeter.

DESCRIPTION OF THE INVENTION

Figure 1:
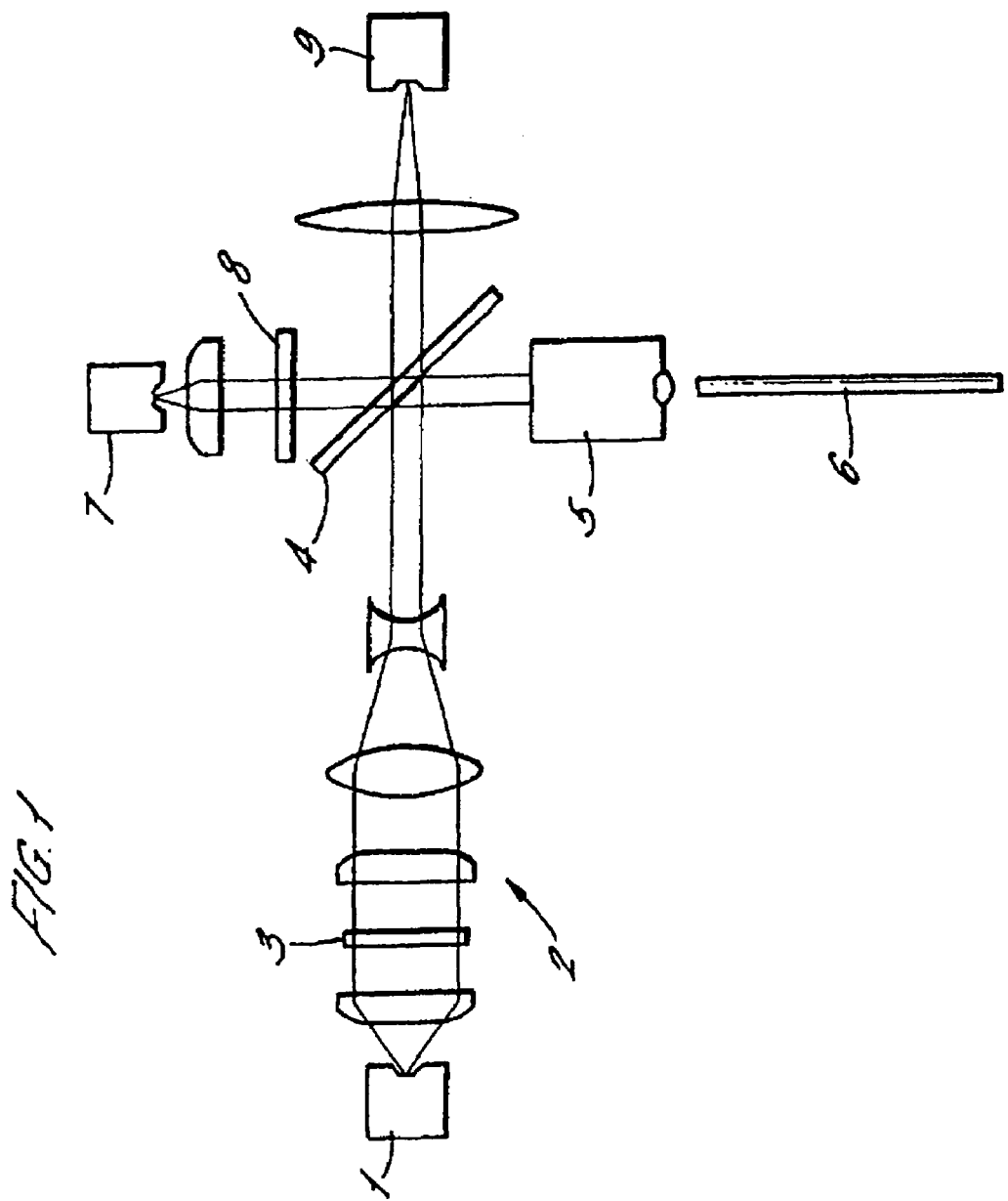
FIG. 1 is a schematic diagram of the optical part of the fibre optic fluorimeter.

Accordingly, in a first aspect the present invention provides a sensor for the in vivo measurement of an analyte, comprising a plurality of particles of suitable size such that when implanted in the body of a mammal the particles can be ingested by macrophages and transported away from the site of implantation, each particle containing the components of an assay having a readout which is an optical signal detectable or measurable transdermally by external optical means, and either each particle being contained within a biodegradable material preventing ingestion by macrophages, or each particle being non-biodegradable.

The sensor particles are preferably embedded within a matrix of biodegradable material, but may alternatively be retained by an envelope of biodegradable material, or may be separately covered with biodegradable material.

Preferably, the particles are less than 5 µm in their largest dimension.

The sensor may be introduced within the skin by injection, preferably using a syringe, or by other methods, in particular by any methods described in WO00/02048. The sensor may be introduced within the thickness of the dermis, or subdermally, or may be introduced to the epidermis, although in the latter case it would be likely to be expelled from the skin by outgrowth of the epidermal layers, possibly before the biodegradable material, if present, has degraded.

Because the sensor is located within the skin, an optical signal generated in the sensor particles can be detected transcutaneously (i.e. through the higher layer(s) of the skin) thus obviating the need for any direct connection between the sensor and the external environment. Once the sensor is in place in a cutaneous location analyte measurements can be taken as often as is necessary with no adverse effects. This is a particular advantage in relation to the long-term care of diabetic patients because if glucose measurements are taken more frequently, tighter control can be maintained over the level of glucose in the blood and the risk of developing conditions related to poorly regulated blood glucose, such as retinopathy, nephropathy, neuropathy, general micro- and macrovascular damage and poor circulation, will be reduced.

The biodegradable material if present and sensor particles are preferably permeable to body fluid, thereby allowing analytes such as glucose to enter the particles by diffusion and to interact with the components of the assay.

Because the sensor of the invention does not itself contain any of the optical components required to interrogate the readout of the assay (these being provided separately and located outside the body) the sensor can easily be provided in a form which is injectable with minimal discomfort to the patient.

The biodegradable material may be an injectable formulation that forms a gel at the point of injection within the skin of the patient. The sensor particles may be formed from a solid polymeric material incorporating the components of the assay which is again injected or implanted cutaneously, the polymeric material typically being of a size suitable for injection through a narrow gauge needle to minimise the discomfort to the patient. When placed cutaneously the solid polymeric material absorbs water and expands to form a gel, thus hydrating the components of the assay.

The biodegradable material may contain the sensor particles such that they are held in position at the site of injection. This enables optical measurements to be taken at the skin surface over this position. The assay contained in all sensor particles may thus be interrogated simultaneously, to give a measureable signal.

The biodegradable material, if present, will degrade over a period of time within the skin, releasing the sensor particles. At this point the useful lifetime of the sensor is over, and it is desirable to remove the particles from the body or to contain the particles within the body away from the sensing site. If the particles are to be removed from the body, it is desirable to achieve this non-surgically.

Macrophage cells occur in the body as part of the immune system. These cells are produced in the bone marrow, and are capable of ingesting foreign particles (including necrotic cells) by surrounding such particles with extrusions of the cell membrane in a process called phagocytosis. Macrophages also secrete enzymes which damage foreign organisms.

Macrophages are able to ingest and transport particles up to a certain size, e.g. 5 µm in largest dimension. Therefore, when the sensor biodegradable material of this invention degrades to release suitably small sensor particles, the sensor particles will be ingested by macrophages. The sensor particles may also be ingested by other components of the immune system.

Alternatively, if the sensor particles are not contained within a biodegradable material, the sensor particles will be ingested by macrophages without a delay for degradation of the biodegradable material. Optical measurements must thus be taken in the relatively short period between introduction of the sensor particles to the body and removal of the sensor particles by macrophages.

Preferably, the sensor particles of the invention have suitable surface characteristics for ingestion by macrophages.

Following phagocytosis, macrophages travel to the lymphatic system. If the sensor particles are biodegradable, their components will be removed by the lymphatic system. If the sensor particles are not biodegradable, they will remain in the lymph nodes. This means that the reagents of the invention will be eliminated via the lymphatic system rather than being released in the skin.

The particles contained within biodegradable material of the present invention may be biodegradable or hydrolysable in vivo, such that they may be digested by macrophages, but this is not necessary. It is undesirable that the particles degrade before they are ingested by macrophages, since this may expose the bloodstream to the assay reagent materials.

Each of the sensor particles may contain the assay components either encapsulated inside a hollow microparticle, or dispersed within the material of a solid microparticle. Techniques for forming such microparticles are known in the art. Typically, assay components, polymer and solvent are combined to form a droplet. The solvent is removed and the droplets are collected, dried and filtered to product a dry, free-flowing powder of solid microparticles containing dispersed assay components. Alternatively, emulsion or coacervation techniques may be used. Both processes may incorporate stabilisation techniques.

Alternatively, for particles contained within biodegradable material, liposomes containing the assay components can be used. In a further embodiment, each sensor particle comprises an empty erythrocyte which has been loaded with assay components. Empty erythrocytes, also known as erythrocyte ghosts, can be prepared by exposing intact erythrocytes to a hypotonic solution so that they swell and burst to release their cytoplasmic contents. The empty erythrocytes can then be loaded with assay components before allowing the plasma membranes to reseal.

Materials suitable as biodegradable materials of a sensor of the invention include biodegradable block copolymers such as those described by Jeong et al., Nature 388: pp 860–862. Aqueous solutions of these materials are thermosensitive, exhibiting temperature-dependent reversible gel-sol transitions. The polymer biodegradable material can be loaded with the sensor particles at an elevated temperature where the material forms a sol. In this form the material is injectable and on cutaneous injection and subsequent rapid cooling to body temperature the material forms a gel matrix. The sensor particles are suspended within this gel matrix which thus constitutes a sensor suitable for detecting or measuring analytes in body fluid. Low molecular weight analytes, such as glucose, can freely diffuse into the gel matrix from the surrounding body fluid. Cutaneous injection of the sol phase material causes neither significant pain or tissue damage.

As an alternative to the gel based sensor described above the sensor may comprise a solid or gel-like polymer biodegradable material within which the sensor particles are distributed. When injected or implanted cutaneously this solid polymer sensor hydrates and swells, and analyte penetrates through the structure to encounter the sensor particles.

Biodegradable materials suitable for use in the construction of the sensors include cross-linked proteins such as human albumin, fibrin gels, polysaccharides such as starch or agarose, polylactides (PLA) such as poly (DL-lactide), polyglycolides (PGA) such as poly (DL-glycolide), poly (lactide-co-glycolides) (PLGA), polyanhydrides, polyorthoesters, fatty acid/cholesterol mixtures that form semi-solid derivates, hyaluronates and liquid crystals of monoolein and water. These materials have the advantage that they are broken down into biologically acceptable molecules which are metabolised and removed from the body via normal pathways.

In the preferred embodiments of the sensor, it is advantageous for the assay components to have a restricted diffusion in order to minimise their loss from the sensor particles into the biodegradable material and potentially into the bloodstream. This can be achieved by ensuring that the sensor particles have a pore size that permits the diffusion of low molecular weight analytes such as glucose, but not diffusion of the assay components themselves. The assay components are preferably of high molecular weight, such as proteins or polymers, in order to restrict their loss from the sensor particles.

Assays suitable for use in the sensor include reactions such as hydrolysis and oxidation leading to detectable optical change i.e. fluorescence enhancement or quenching which can be observed transcutaneously. A preferred assay for use in the sensor of the invention is a binding assay, the readout of which is a detectable or measurable optical signal which can be interrogated transcutaneously using optical means. The binding assay generating the optical signal should preferably be reversible such that a continuous monitoring of fluctuating levels of the analyte can be achieved. This reversibility is a particular advantage of the use of a binding assay format in which the components of the assay are not consumed. Binding assays are also preferred for use in the sensor of the invention for reasons of safety as they cannot generate any unwanted products as might be generated by an enzymatic or electrochemical reaction.

Preferred binding assay configurations for use in the sensor of the invention include a reversible competitive, reagent limited, binding assay, the components of which include an analyte analog and an analyte binding agent capable of reversibly binding both the analyte of interest and the analyte analog. The analyte of interest and the analyte analog compete for binding to the same binding site on the analyte binding agent. Such competitive binding assay configurations are well known in the art of clinical diagnostics and are described, by way of example, in The Immunoassay Handbook, ed. David Wild, Macmillan Press 1994. Suitable analyte binding agents for use in the assay would include antibodies or antibody fragments which retain an analyte binding site (e.g. Fab fragments), lectins (e.g. concanavalin A), hormone receptors, drug receptors, aptamers and molecularly-imprinted polymers. Preferably, the analyte analog should be a substance of higher molecular weight than the analyte such that it cannot freely diffuse out of the sensor particles. For example, an assay for glucose might employ a high molecular weight glucose polymer such as dextran as the analyte analog.

Suitable optical signals which can be used as an assay readout in accordance with the invention include any optical signal which can be generated by a proximity assay, such as those generated by fluorescence resonance energy transfer, fluorescence polarisation, fluorescence quenching, phosphorescence technique, luminescence enhancement, luminescence quenching, diffraction or plasmon resonance, all of which are known per se in the art.

The most preferred embodiment of the sensor of the invention incorporates a competitive, reagent limited binding assay which generates an optical readout using the technique of fluorescence resonance energy transfer. In this assay format, the analyte analog is labelled with a first chromophore and the analyte binding agent is labelled with a second chromophore. One of the first and second chromophores acts as a donor chromophore and the other acts as an acceptor chromophore. It is an essential feature of the assay that the fluorescence emission spectrum of the donor chromophore overlaps with the absorption spectrum of the acceptor chromophore, such that when the donor and acceptor chromophores are brought into close proximity by the binding agent a proportion of the energy which normally would produce fluorescence emitted by the donor chromophore (following irradiation with incident radiation of a wavelength absorbed by the donor chromophore) will be non radiatively transferred to the adjacent acceptor chromophore, a process known in the art as fluorescence resonance energy transfer, with the result that a proportion of the fluorescent signal emitted by the donor chromophore is quenched, that the lifetime of the fluorescence is changed, and, in some instances, that the acceptor chromophore emits fluorescence. The acceptor chromophore may, however, be a non-fluorescent dye. Fluorescence resonance energy transfer will only occur when the donor and acceptor chromophores are brought into close proximity by the binding of analyte analog to analyte binding agent. Thus, in the presence of analyte, which competes with the analyte analog for binding to the analyte binding agent, the amount of quenching is reduced (resulting in a measurable increase in the intensity of the fluorescent signal emitted by the donor chromophore or a fall in the intensity of the signal emitted by the acceptor chromophore) as labelled analyte analog is displaced from binding to the analyte binding agent. The intensity or lifetime of the fluorescent signal emitted from the donor chromophore thus correlates with the concentration of analyte in the subcutaneous fluid bathing the sensor.

An additional advantageous feature of the fluorescence resonance energy transfer assay format arises from the fact that any fluorescent signal emitted by the acceptor chromophore following excitation with a beam of incident radiation at a wavelength within the absorption spectrum of the acceptor chromophore is unaffected by the fluorescence resonance energy transfer process. It is therefore possible to use the intensity of the fluorescent signal emitted by the acceptor chromophore as an internal reference signal, for example in continuous calibration of the sensor or to monitor the extent to which the sensor has degraded and thus indicate the need to implant or inject a fresh sensor. As the sensor biodegradable material degrades and sensor particles are released, the amount of acceptor chromophore present in the sensor will decrease, and hence the intensity of fluorescent signal detected upon excitation of the acceptor chromophore will also decrease. The fall of this signal below an acceptable baseline level would indicate the need to implant or inject a fresh sensor. Competitive binding assays using the fluorescence resonance energy transfer technique which are capable of being adapted for use in the sensor of the invention are known in the art. U.S. Pat. No. 3,996,345 describes immunoassays employing antibodies and fluorescence resonance energy transfer between a fluorescer-quencher chromophoric pair. Meadows and Schultz (Anal. Chim. Acta (1993 280: pp 21–30) describe a homogeneous assay method for the measurement of glucose based on fluorescence resonance energy transfer between a labelled glucose analog (FITC labelled dextran) and a labelled glucose binding agent (rhodamine labelled concanavalin A). In all of these configurations the acceptor and donor chromophores/quenchers can be linked to either the binding agent or the analyte analog.

The various FRET chemistries described in the background art cited in the introduction of this document may be used.

Fluorescence lifetime or fluorescence intensity measurements may be made. As described in Lakowitz et al., fluorescence lifetime may be measured by phase modulation techniques.

An alternative to the fluorescence resonance energy transfer is the fluorescence quenching technique. In this case a compound with fluorescence quenching capability is used instead of the specific acceptor chromophore and the optical signal in a competitive binding assay will increase with increasing analyte. An example of a powerful and non-specific fluorescence quencher is given by Tyagi et al. Nature Biotechnology (1998) 18: p 49.

The sensor of the invention can be adapted for the detection or quantitative measurement of any analyte present in body fluid. Preferred analytes include glucose (in connection with the long-term monitoring of diabetics), urea (in connection with kidney disease or dysfunction), lactate (in connection with assessment of muscle performance in sports medicine), ions such as sodium, calcium or potassium and therapeutic drugs whose concentration in the blood must be closely monitored, such as, for example, digoxin, theophylline or immunosuppressant drugs. The above analytes are listed by way of example only and it is to be understood that the precise nature of the analyte to be measured is not material to the invention.

The sensor is interrogated transcutaneously using optical means i.e. no physical connection is required between the sensor and the optical means. When the sensor incorporates a competitive, reagent limited, binding assay employing the technique of fluorescent energy transfer, the optical means should supply a first beam of incident radiation at a wavelength within the absorption spectrum of the donor chromophore and preferably a second beam of incident radiation at a wavelength within the adsorption spectrum of the acceptor chromophore. In addition, the optical means should preferably be capable of measuring optical signals generated in the sensor at two different wavelengths; wavelength 1 within the emission spectrum of the donor chromophore (the signal generated in connection with the measurement of analyte and wavelength 2 in the emission spectrum of the acceptor chromophore (which could be the analyte signal or the internal reference or calibration signal).

Optical means suitable for use in remote interrogation of the device of the invention include a simple high-throughput fluorimeter comprising an excitation light source such as, for example, a light-emitting diode (blue, green or red), an excitation light filter (dichroic or dye filter) and a fluorescent light detector (PIN diode configuration). A fluorimeter with these characteristics may exhibit a sensitivity of between picomolar to femtomolar fluorophore concentration.

A suitable fluorimeter set-up is shown in the accompanying FIG. 1 and described in the Examples included herein. The fluorimeter separately measures the following parameters:

At wavelength 1 (donor chromophore)
Excitation light intensity, $I(1,0)$
Ambient light intensity, $I(1,1)$
Intensity of combined fluorescent and ambient light, $I(1,2)$
At wavelength 2 (acceptor chromophore)
Excitation light intensity, $I(2,0)$
Ambient light intensity, $I(2,1)$
Intensity of combined fluorescent and ambient light, $I(2,2)$ Measurements are taken by holding the fluorimeter close to the skin and in alignment with the sensor. When making transcutaneous measurements of the fluorescent signals generated in the sensor it is necessary to take account of the absorption of signal by the skin, the absorptivity of human skin is found by experiment to be lowest in the range from 400 nm to 900 nm. The final output provided is the normalised ratio between the fluorescent intensity from the two fluorophores, defined by the following relation (Equation 1)

Final output=$(I(1,2)-I(1,1))*I(2,0)/(I(2,2)-I(2,1))*I(1,0)$ (1)

The final output from the optical means (e.g. the fluorimeter) as given by Equation 1 above is converted to analyte concentration preferably by means of a computer using calibration data which can be obtained based on the principles set out below.

A calibration curve can be established empirically by measuring response versus analyte concentration for a physiologically relevant range of analyte concentrations. Preferably, this takes place in vitro as part of the production of the sensor device. The calibration procedure can be simplified considerably by using the mathematical relation between response and analyte concentration in a competitive affinity sensor which is derived as follows:

The response of a competitive affinity sensor is governed by the reactions:

$RC \leftrightarrow R+C$ $RL \leftrightarrow R+L$

Designating the dissociation of the complexes RC and RL, formed by the combination of analyte binding agent (R) with analyte (L) or analyte analog (C).

The corresponding dissociation equilibrium constants are:

$$K_1 = \frac{C_r C_c}{C_{RC}}$$

and, $$K_2 = \frac{C_r C_c}{C_{RL}}$$

where C designates the number of moles of the species in the sensor divided by the sensor volume. Using this measure of concentration both immobilised species and species in solution are treated alike.

The mass balance equations are:

$T_C = C_C + C_{RC}$ for total analyte analog concentration and, $T_R = C_R + C_{RC} + C_{RL}$ for total analyte binding agent concentration.

Using the expression above, the relation between response and analyte concentration is derived:

$$\frac{T_C - C_C}{C_C} K_1 = \frac{T_R - (T_C - C_C)}{1 + (C_L/K_2)}$$ (2)

By using this relation the amount of data necessary for the calibration can be reduced to two key parameters: Total analyte binding agent concentration and total analyte analog concentration. The calibration curve is thus determined by two points on the curve.

In a second aspect, the present invention relates to a process for the detection of an analyte using a sensor as described herein, comprising implantation of the sensor into the skin of a mammal, transdermal detection or measurement of analyte using external optical means, degradation of the biodegradable material, ingestion of the particles by macrophages, and removal of the particles from the site of implantation by macrophages.

EXAMPLE 1

A glucose assay according to Meadows and Schultz (Talanta, 35, 145–150, 1988) was developed using concanavalin A-rhodamine and dextran-FITC (both from Molecular Probes Inc., Oregan, USA). The principle of the assay is fluorescence resonance energy transfer between the two fluorophores when they are in close proximity; in the presence of glucose the resonance energy transfer is inhibited and the fluorescent signal from FITC (fluorescein) increases. Thus increasing fluorescence correlates with increasing glucose. The glucose assay was found to respond to glucose, as reported by Schultz, with approximately 50 percent recovery of the fluorescein fluorescence signal at 20 mg/dL glucose. Fluorescence was measured in a Perkin Elmer fluorimeter, adapted for flow-through measurement using a sipping device.

EXAMPLE 2

The sensor particles are produced by combining concanavalin A-rhodamine and dextran-FITC with polymer and solvent to form a droplet. The solvent is removed, and the droplets are collected, dried and filtered to give a dry, free-flowing powder.

The sensor particles are combined with biodegradable material in an injectable formulation to form the sensor.

EXAMPLE 3

Malachite Green (MG)-Dextran is prepared using the method described in Joseph R. Lakowicz et al., Analytica Chimica Acta, 271 (1993) 155–164. Amino dextran (10 000 MW) is dissolved in pH 9.0 bicarbonate buffer and reacted with an 10-fold excess of MG-isothiocyanate for 4 h at room temperature. The labelled dextran is freed from excess fluorophore on a Sephadex G-50 column.

Cascade Blue Concanavalin A (Cascade Blue-Con A) is obtained from Sigma.

The sensor particles are produced by combining Cascade Blue-Concanavalin A and Malachite Green-Dextran with polymer and solvent to form a droplet. The solvent is removed, and the droplets are collected, dried and filtered to give a dry, free-flowing powder.

The sensor particles are combined with biodegradable material in an injectable formulation to form the sensor.

EXAMPLE 4

A fibre optic fluorimeter was assembled as follows:

The optical part of a fibre optic fluorimeter was made from standard components on a micro bench. The set-up, comprising a red LED as light source, lenses, dichroic beamsplitter and filters and detector diodes, was as shown in FIG. 1. Briefly, the fluorimeter comprises a light emitting diode (1) providing an excitation light beam which passes through a condenser (2) containing an excitation filer (3) and is incident upon a beamsplitter (4). Part of the excitatory beam is thereby deflected into launching optics (5) and enters an optical fibre (6). When the fluorimeter is in use in the interrogation of a cutaneously located sensor the end of the skin, in alignment with the cutaneous sensor, so that beam of excitatory light is incident upon the sensor a portion of the optical signal emitted from the sensor following excitation enters the optical fibre (6) and is thereby conveyed into the fluorimeter where it passes through a blocking diode (7). The fluorimeter also contains a reference detector diode (9) which provides a reference measurement of the excitatory light emitted from the LED (1). The ends of a 1 m long Ensign Beckford optical fibre, 0.5 mm in diameter, numerical aperture of 0.65, were ground to a mirror finish using diamond paste on glass paste. One end of the fibre was mounted in an X Y Z holder in front of a 20× microscope objective. The diodes (LED (1) and detector diodes (7) and (9)) were connected to a custom made driver/amplifier circuit as shown in FIG. 2. The circuit comprises a sender (10), current amplifiers (11) and (12), multiplexers (13) and (14), integrators (15) and (16) and analog divider (17). The driver circuit was set to drive the LED (1) at 238 Hz and the signals from the detector diodes (7) and (9) were switched between ground and the storage capacitors (integrator with a time constant of 1 second) synchronised with the drive signal. The two integrated signals correspond to background-corrected fluorescent signal and background corrected excitation light level (LED intensity). The former divided by the latter was supported by an analog divider as shown in FIG. 2. For test purposes, the distal end of the fibre (6) was dipped into dilute solutions of rhodamine and the optics were adjusted for maximum signal from the analog divider.

The fluorimeter is battery operated (typical power consumption 150 mA at 9 V) and for convenience can be constructed in the shape and dimensions of a pen.

EXAMPLE 5

The sensor prepared in Example 2 is injected by syringe in the back of the hand of a human volunteer.

A fibre optic fluorimeter (see Example 4) is directed at the skin and a rhodamine fluorescence lifetime signal is obtained and correlated with a conventional blood glucose measurement indicating that transdermal measurements can be made on implanted sensors.

The invention claimed is:

1. A sensor for in vivo measurement of an analyte, comprising a plurality of particles having a size such that when implanted in a body of a mammal at an implantation site the particles can be ingested by macrophages and transported away from the implantation site, wherein each particle of the sensor contains the components of an assay having a readout which is an optical signal detectable transdermally by external optical means, and wherein the particles are each contained within a biodegradable material preventing ingestion by the macrophages.

2. A sensor as claimed in claim 1, wherein the particles are less than 5 μm in their largest dimension.

3. A sensor as claimed in claim 1, wherein the assay is a binding assay.

4. A sensor as claimed in claim 3, wherein the binding assay is a competitive binding assay, the components of which include an analyte binding agent and an analyte analogue.

5. A sensor as claimed in claim 4, wherein the analyte analogue is labelled with a first chromophore and the analyte binding agent is labelled with a second chromophore, an emission spectrum of the first chromophore or the second chromophore overlapping with an absorption spectrum of the second chromophore or the first chromophore respectively.

6. A sensor as claimed in claim 4, wherein the binding agent is an antibody, a Fab fragment, a lectin, a hormone receptor, a drug receptor, an aptamer or a molecularly-imprinted polymer.

7. A sensor as claimed in claim 1, wherein the optical signal is generated by fluorescence resonance energy transfer, fluorescence polarisation, fluorescence quenching, phosphorescence, luminescence enhancement, luminescence quenching, diffraction or plasmon resonance.

8. A sensor as claimed in claim 1, wherein the analyte is glucose.

9. A sensor as claimed in claim 1, wherein the optical signal is quantitatively measurable.

10. A process for the detection of an analyte using a sensor as claimed in claim 1, comprising the steps of:
    implanting the sensor into skin of a mammal at an implantation site, and
    transdermally detecting analyte using external optical means,
    where implantation is followed by degradation of the biodegradable material, ingestion of the particles by macrophages, and removal of the particles from the implantation site.

11. A sensor for in vivo measurement of an analyte, comprising a plurality of particles having a size such that when implanted in a body of a mammal at an implantation site the particles can be ingested by macrophages and transported away from the implantation site, wherein each particle of the sensor contains the components of an assay having a readout which is an optical signal detectable transdermally by external optical means, and wherein the particles are each contained within a biodegradable material preventing ingestion by the macrophages, the biodegradable material being a gel.

* * * * *